US009162000B2

(12) United States Patent
Ullman

(10) Patent No.: US 9,162,000 B2
(45) Date of Patent: Oct. 20, 2015

(54) FOOTWEAR SANITIZING AND DEODORIZING SYSTEM

(71) Applicant: Shoe Care Innovations, Inc., Redwood City, CA (US)

(72) Inventor: Adam Ullman, Menlo Park, CA (US)

(73) Assignee: Shoe Care Innovations, Inc., Redwood City, CA (US)

( * ) Notice: Subject to any disclaimer, the term of this patent is extended or adjusted under 35 U.S.C. 154(b) by 0 days.

(21) Appl. No.: 14/552,150

(22) Filed: Nov. 24, 2014

(65) Prior Publication Data

US 2015/0076369 A1  Mar. 19, 2015

Related U.S. Application Data

(63) Continuation of application No. 13/920,055, filed on Jun. 17, 2013, now Pat. No. 8,895,938, which is a continuation-in-part of application No. 13/160,066, filed on Jun. 14, 2011, now Pat. No. 8,466,433, which (Continued)

(51) Int. Cl.
*H01J 37/20* (2006.01)
*A61L 2/10* (2006.01)
*A61L 2/08* (2006.01)
*A61L 9/20* (2006.01)

(52) U.S. Cl.
CPC . *A61L 2/10* (2013.01); *A61L 2/088* (2013.01); *A61L 9/205* (2013.01); *A61L 2209/11* (2013.01); *A61L 2209/12* (2013.01)

(58) Field of Classification Search
CPC ............... A61L 2/10; A61L 2/24; A61L 2/26; A43D 3/1491; A43D 3/1433

USPC ............ 250/455.11, 504 R, 504 H; 12/114.2, 12/117.4, 128

See application file for complete search history.

(56) References Cited

U.S. PATENT DOCUMENTS

| 1,358,963 | A |   | 11/1920 | McGrath |
| 1,733,611 | A |   | 10/1929 | Lessard |
| 2,070,858 | A | * | 2/1937  | Des Jardins et al. .......... 219/523 |
| 2,201,548 | A | * | 5/1940  | Treinis ..................... 250/455.11 |

(Continued)

FOREIGN PATENT DOCUMENTS

| JP | 63-136569 | 6/1988 |
| JP | 5-62248   | 8/1993 |

(Continued)

OTHER PUBLICATIONS

"What is Oxititan," http://web.archive.org/web/20120327042817/http://www.oxititan.com/what-is-oxititan/, (2 pages) retrieved on Dec. 12, 2013.

*Primary Examiner* — Michael Maskell
(74) *Attorney, Agent, or Firm* — Stoel Rives LLP

(57) ABSTRACT

Introducing ultraviolet (UV) light to activate a light sensitive chemical compound applied to interior portions of footwear alters the environment inside a shoe or other footwear to destroy microorganisms or inhibit their growth. Visible light can also be used to prevent further microorganism growth. Introducing forced air flow through the footwear removes dampness in and thereby deodorizes the footwear. A preferred embodiment comprises an adjustable shoe tree equipped with a UV germicidal light source and electronic safeguards that prevent appreciable leakage of UV radiation outside the shoe.

14 Claims, 15 Drawing Sheets

Related U.S. Application Data is a continuation-in-part of application No. 12/281,910, filed as application No. PCT/US2007/063925 on Mar. 13, 2007, now Pat. No. 7,960,706.

(60) Provisional application No. 60/881,552, filed on Jan. 22, 2007, provisional application No. 60/781,276, filed on Mar. 13, 2006.

(56) References Cited

U.S. PATENT DOCUMENTS

| | | | | |
|---|---|---|---|---|
| 2,246,135 | A | * | 6/1941 | Homer ................. 250/455.11 |
| 2,269,006 | A | | 1/1942 | Clark |
| 2,350,091 | A | * | 5/1944 | Bergman ............. 250/455.11 |
| 2,413,494 | A | | 12/1946 | Fortney |
| 2,481,930 | A | * | 9/1949 | Katchel ................. 12/129.4 |
| 2,510,315 | A | * | 6/1950 | Malberg ................ 12/117.4 |
| 2,569,079 | A | * | 9/1951 | Special ................ 250/455.11 |
| 3,078,526 | A | * | 2/1963 | Caruso ................. 422/186 |
| 3,417,494 | A | * | 12/1968 | Claff ..................... 36/44 |
| 3,772,722 | A | | 11/1973 | Gellert |
| 3,970,856 | A | | 7/1976 | Mahaffey et al. |
| D245,204 | S | | 7/1977 | Walter |
| 4,517,443 | A | | 5/1985 | Dollst |
| 4,667,817 | A | | 5/1987 | Im et al. |
| 4,874,129 | A | * | 10/1989 | DiSapio et al. ........... 239/36 |
| 4,981,651 | A | * | 1/1991 | Horng ................... 422/24 |
| D338,323 | S | | 8/1993 | Bramble |
| D411,002 | S | | 6/1999 | Farmer |
| 5,920,075 | A | | 7/1999 | Whitehead |
| D415,268 | S | | 10/1999 | Farmer |
| 5,978,996 | A | * | 11/1999 | Ullman ................. 12/129.4 |
| D417,727 | S | | 12/1999 | Christianson |
| D418,670 | S | | 1/2000 | Wilcox |
| 6,123,906 | A | | 9/2000 | Farmer |
| D437,117 | S | * | 2/2001 | Pinkhasov ............. D3/317 |
| 6,264,887 | B1 | | 7/2001 | Farmer |
| 6,286,235 | B1 | | 9/2001 | An |
| D485,364 | S | | 1/2004 | Lee |
| 6,675,421 | B1 | * | 1/2004 | Hsu .................... 12/129.4 |
| 6,725,571 | B2 | | 4/2004 | Liu |
| D507,341 | S | | 7/2005 | Taylor |
| D581,058 | S | | 11/2008 | Elkerbout |
| 7,449,194 | B2 | * | 11/2008 | Lelah et al. ............. 424/404 |
| 7,741,266 | B2 | * | 6/2010 | Bell et al. .................. 512/1 |
| 8,241,565 | B1 | * | 8/2012 | Abdul .................... 422/24 |
| 2002/0083535 | A1 | * | 7/2002 | Fraden ................. 12/128 B |
| 2004/0099812 | A1 | * | 5/2004 | Humphreys et al. ...... 250/455.11 |
| 2006/0005328 | A1 | * | 1/2006 | Johnson ................. 12/128 R |
| 2006/0017025 | A1 | * | 1/2006 | Jensen .................. 250/504 R |
| 2007/0115681 | A1 | * | 5/2007 | Cooper et al. ............. 362/555 |
| 2008/0052957 | A1 | * | 3/2008 | Taheri ................... 36/7.1 R |

FOREIGN PATENT DOCUMENTS

| | | |
|---|---|---|
| JP | 3007995 | 2/1995 |
| JP | 7-255827 | 10/1995 |
| JP | 11-263322 | 9/1999 |
| JP | 3085286 | 4/2002 |
| KR | 20-2010-0005810 | 6/2010 |
| KR | 20-2011-0001958 | 2/2011 |
| WO | WO-01/47388 A1 | 7/2001 |

* cited by examiner

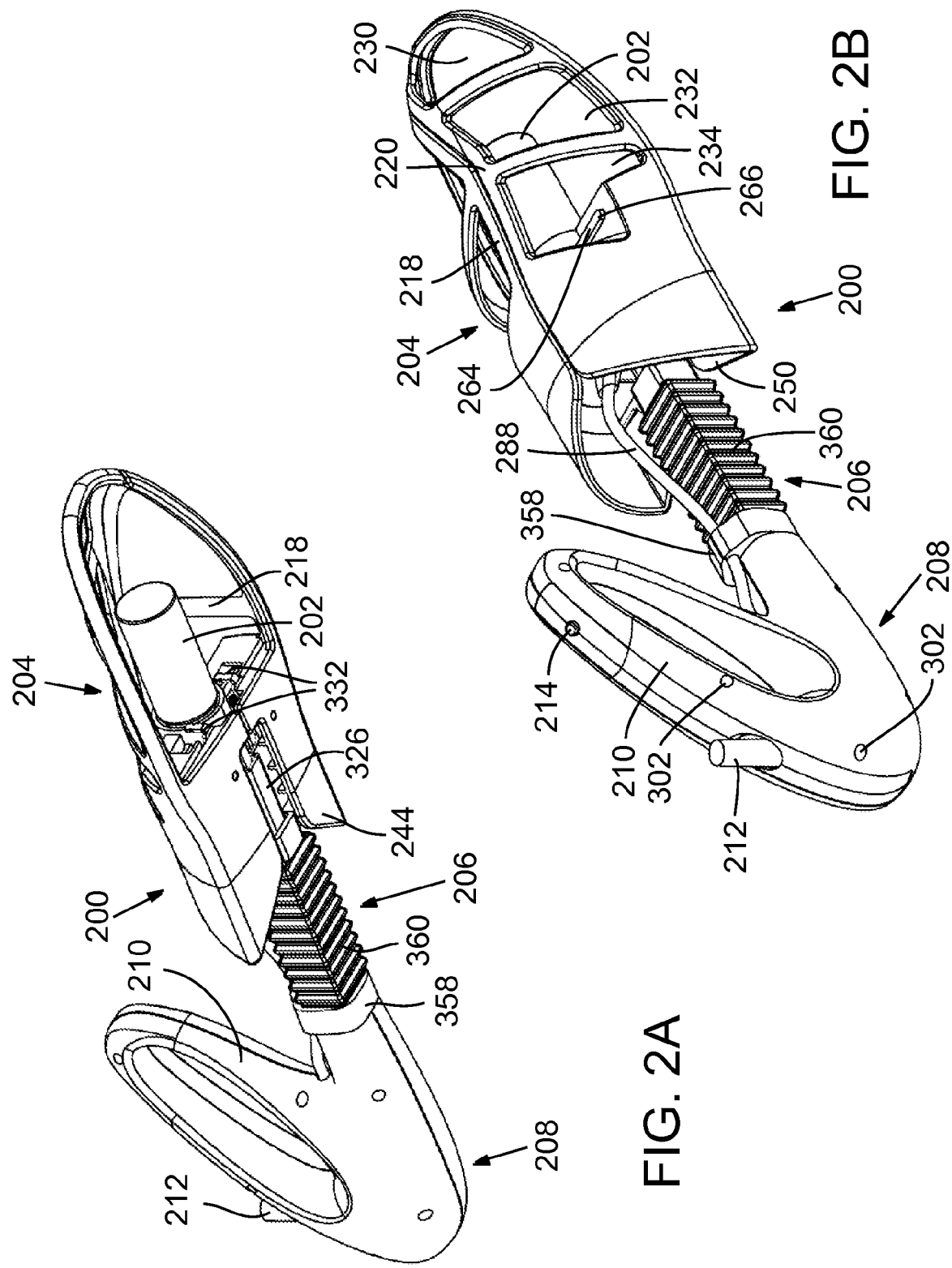

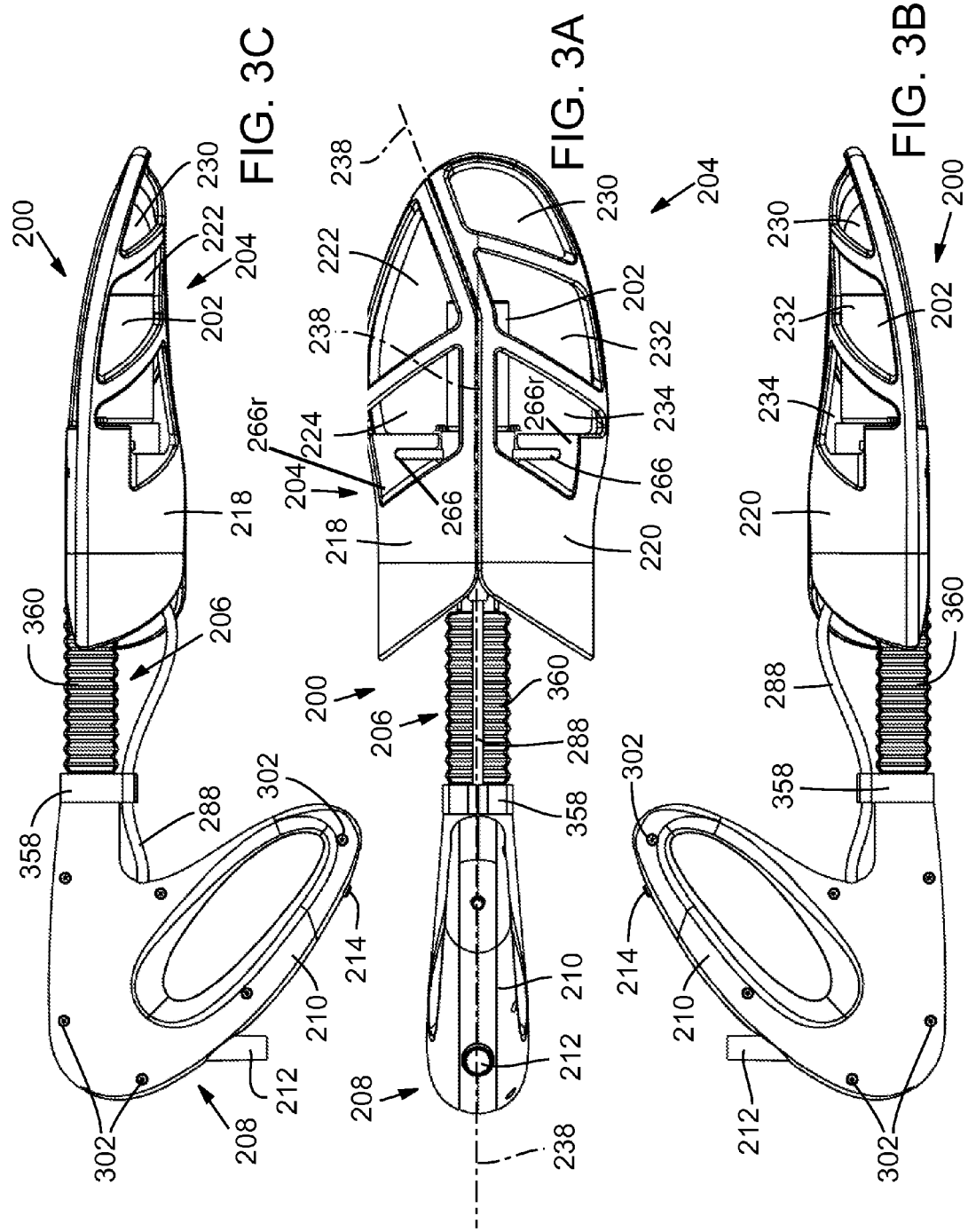

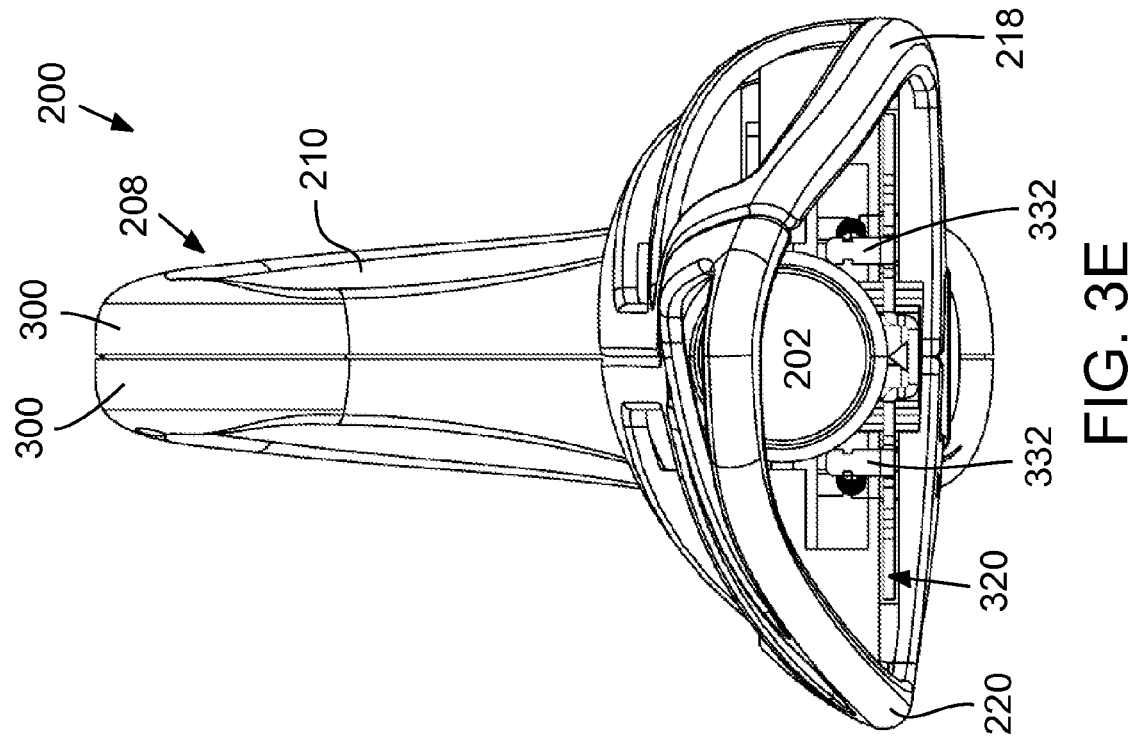
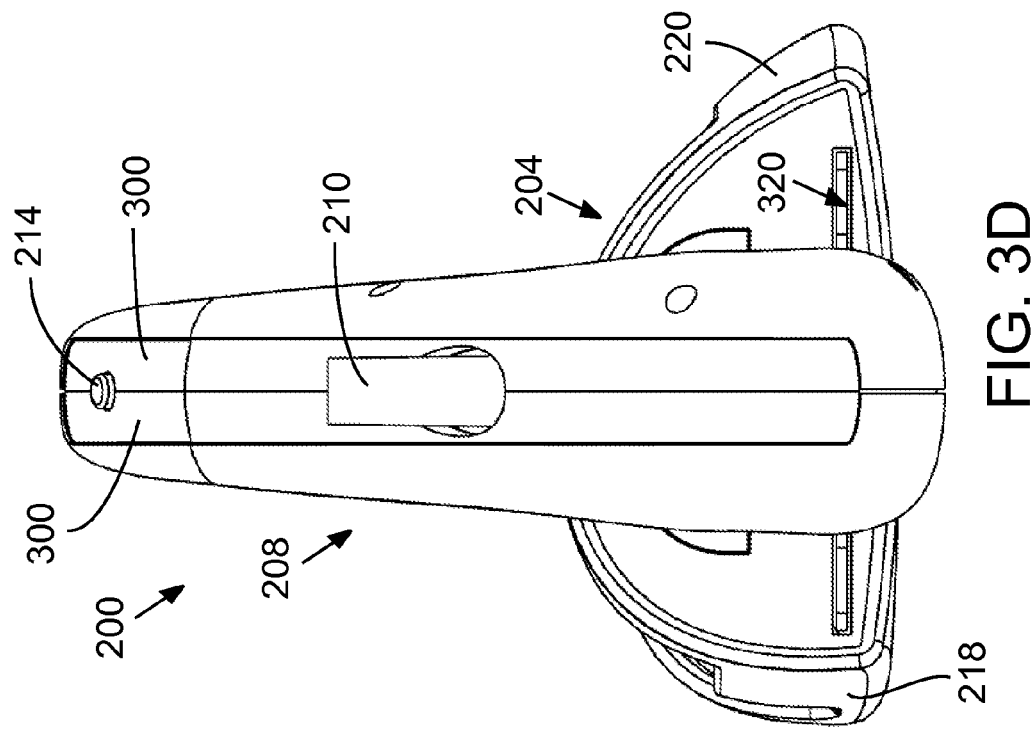

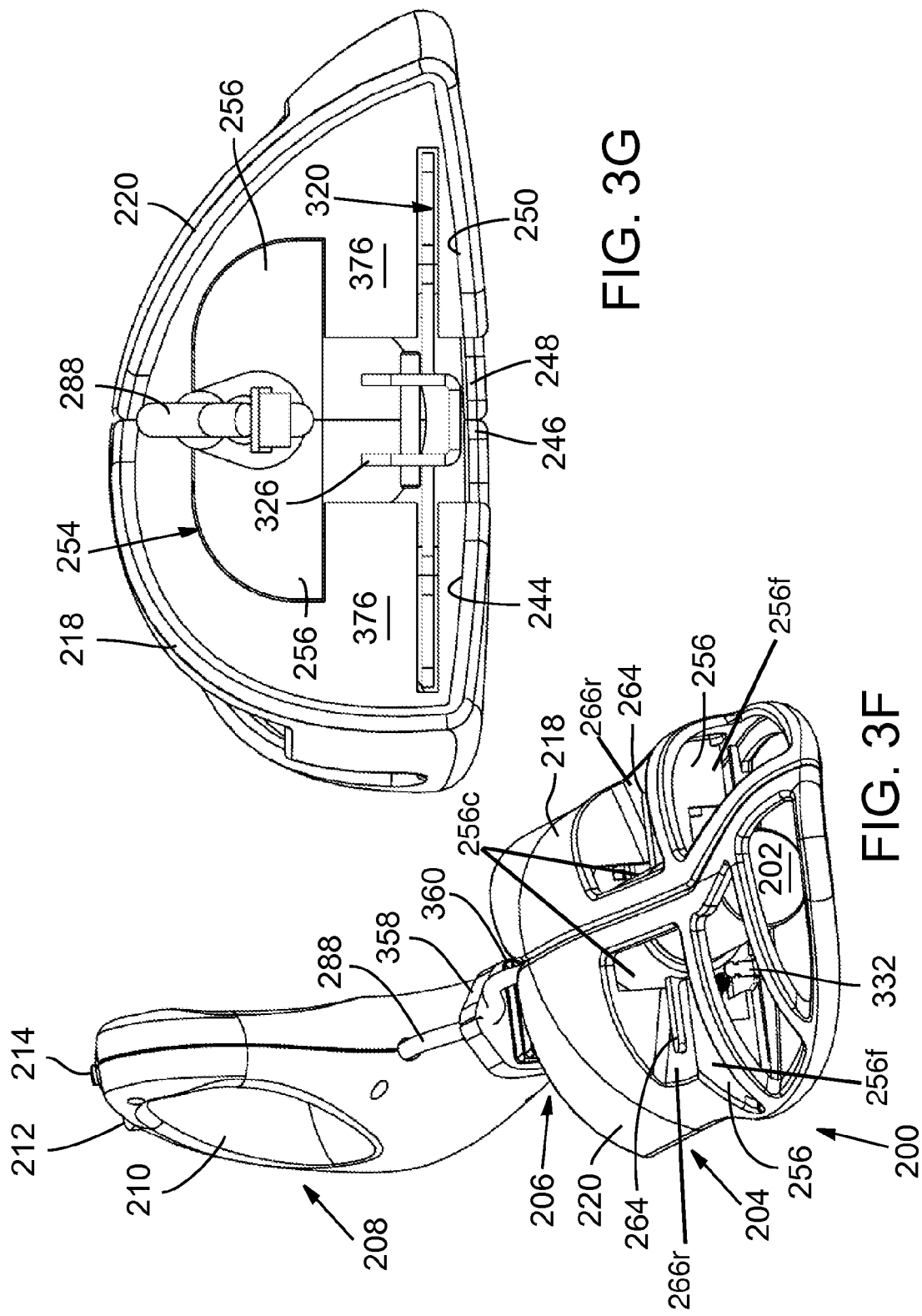

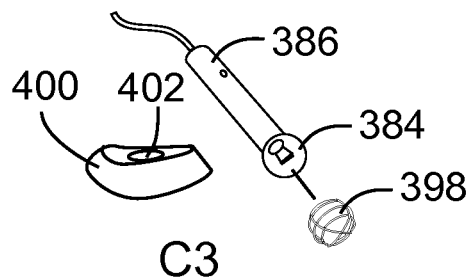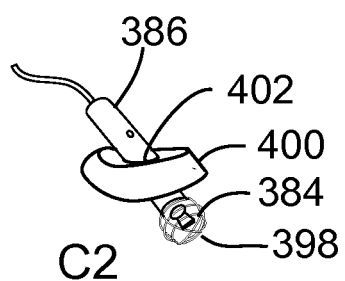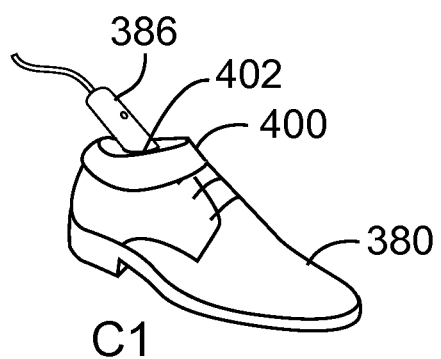
FIG. 9C

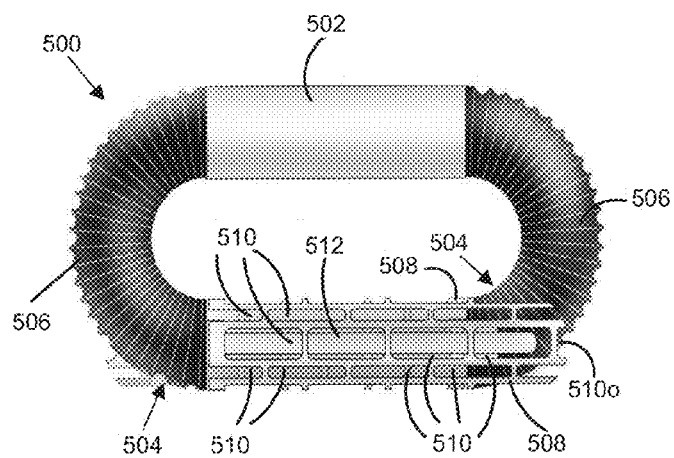
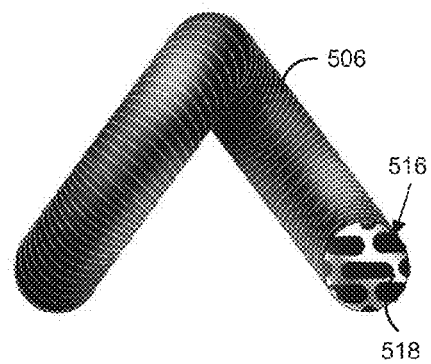
Fig. 10A
Fig. 11
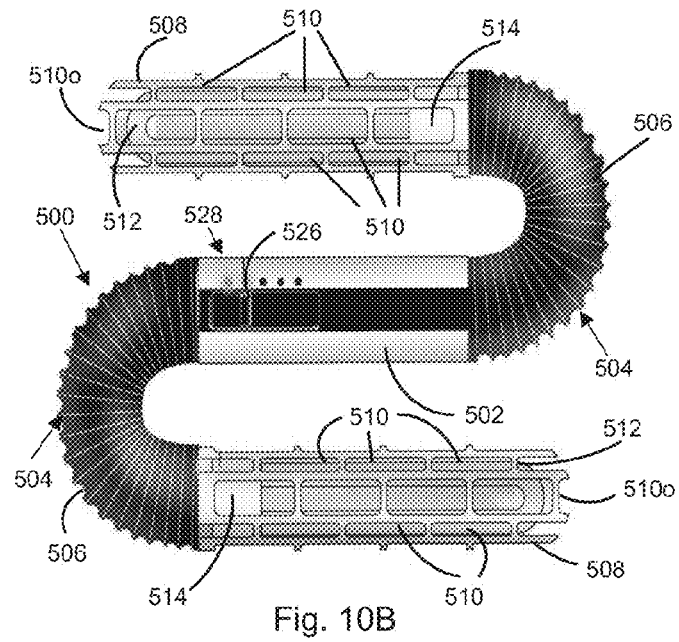
Fig. 10B
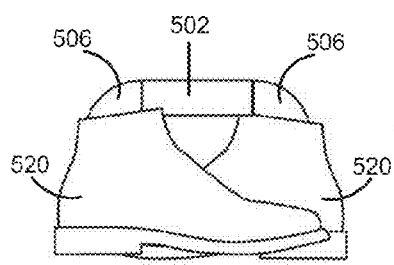
Fig. 12A
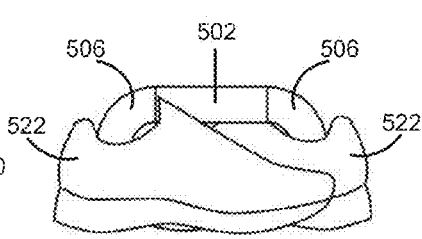
Fig. 12B
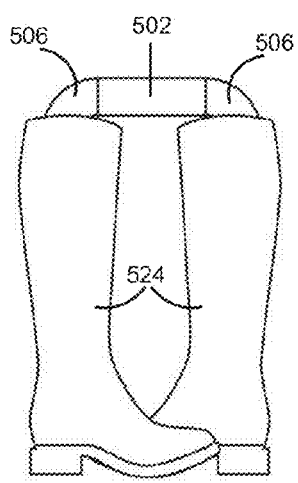
Fig. 12C

FOOTWEAR SANITIZING AND DEODORIZING SYSTEM

RELATED APPLICATIONS

This application is a continuation of U.S. patent application Ser. No. 13/920,055, filed Jun. 17, 2013, and now U.S. Pat. No. 8,895,938; which is a continuation-in-part of U.S. patent application Ser. No. 13/160,066, filed Jun. 14, 2011, and now U.S. Pat. No. 8,466,433; which is a continuation-in-part of U.S. patent application Ser. No. 12/281,910, filed Sep. 5, 2008, and now U.S. Pat. No. 7,960,706; which is a 371 of International Application No. PCT/US07/63925, filed Mar. 13, 2007; which claims benefit of U.S. Provisional Patent Application Nos. 60/781,276 and 60/881,552, filed Mar. 13, 2006 and Jan. 22, 2007, respectively.

COPYRIGHT NOTICE

© 2014 Shoe Care Innovations, Inc. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR §1.71 (d).

TECHNICAL FIELD

The present disclosure pertains to the use of light and forced air flow in sanitizing and deodorizing human footwear.

BACKGROUND INFORMATION

Warm, damp, dark environments provide favorable conditions for growth of infectious biological microorganisms, allowing bacteria, viruses, fungi, and their associated odors to proliferate. For example, foot perspiration within shoes promotes warmth and dampness, while closed shoes stored in dark closets may fail to admit enough broad spectrum ambient light to control pathogen levels. Excessive levels of harmful microorganisms sustained in enclosed shoes may cause or promote various foot maladies.

It is well-known that exposure to ultraviolet (UV) light of certain wavelengths, intensities, and durations can destroy or inhibit growth of surface pathogens. For instance, germicidal lamps that emit UVC radiation are used to treat waste water for the purpose of reducing organic content. U.S. Pat. Nos. 4,981,651 and 5,978,996 describe the use of UV light for sterilization; however, not all UV light wavelengths are germicidal. The UV spectrum spans wavelengths from 10 nm to 400 nm. The band from 320 nm to 400 nm is designated as UVA; 280 nm to 320 nm is UVB; and 100 nm to 280 nm is UVC. Germicidal UV light, the type that destroys microorganisms, is limited to a wavelength range from 240 nm to 280 nm, in which maximum germicidal efficiency coincides with a wavelength of 254 nm. UVA and visible light, which includes a near-UV component, have been shown to inhibit growth but not to destroy pathogens.

One concern with harnessing UV light, which is a form of short wavelength, high energy radiation, is that UV light can cause damage to human tissue. Eyes are especially vulnerable when exposed to direct incidence of UV light. Thus, any application of high energy radiation, including UV light, should protect against unwanted exposure.

Many air filtrations systems have filters to clean the air. A typical air filter is the HEPA filter that is designed to remove pollens, dust, smoke and other tiny particles that may attribute to odor. Additionally, some air filtration systems use carbon to help remove pollutants from the air. Other air filters, such as those described in U.S. Pat. Nos. 7,951,327 and 7,927,554, use titanium dioxide ($TiO_2$), in conjunction with a UV light source, in a process called photo-catalytic oxidation to destroy bacteria, volatile organic compounds, and other airborne pollutants to sanitize the air.

SUMMARY OF THE DISCLOSURE

The present disclosure relates to introducing light and forced air flow to alter the environment inside a shoe or other footwear to destroy microorganisms or to inhibit their growth and to deodorize the footwear. Air circulation helps dry damp environments. Introducing air into or circulating air through a shoe, such as a boot dryer does, assists in removing dampness found inside a shoe. In one embodiment, delivery of germicidal UV light is accomplished by mounting a set of light emitting diodes (LEDs), tuned to an appropriate UV wavelength, inside a hollow shoe tree that is inserted into the toe of the shoe. UV LEDs that emit light within the germicidal range can be used to destroy microorganisms residing in the shoe. In a second embodiment, an alternative light source, a UV germicidal bulb, is used in place of UV LEDs. In a third embodiment, visible light LEDs or a visible light bulb, both of which are less expensive and easier to acquire than germicidal UV light sources, are used because light within the visible spectrum inhibits or prevents further growth of microorganisms, as opposed to actually killing them. In a fourth embodiment, suitable for commercial use, an enclosure contains UV light emanating from a bulb inserted inside a shoe, without the support of a shoe tree. In a fifth embodiment, an enclosure contains visible light emanating from a bulb inserted inside a shoe, without support of a shoe tree.

Embodiments of or accessories associated with a shoe tree are implemented with safeguards to contain UV radiation exposure within a region of interest. One method of containing UV radiation inside a shoe entails placing an opaque or a translucent barrier between the propagation path of the UV radiation and openings in the shoe. A preferred embodiment of such a barrier is a seal set around the spine or heel of a shoe tree. Alternatively, the forepart of a shoe tree may incorporate a light restrictor, or caps may be placed over openings in the shoe.

Another method of preventing unwanted UV exposure entails activating the UV light source only if a threshold level of ambient light is not detected. Ambient light detected inside a shoe indicates a light leak, which could allow UV radiation to escape. A light leak could be the result of improper insertion of the UV light source into the shoe. Disabling the UV power source when a threshold level of ambient light is detected by a light sensor, such as a photodiode, phototransistor, a charge-coupled device (CCD) sensor or a complementary metal-oxide semiconductor (CMOS) sensor, similar to sensors used in cameras, prevents unwanted UV exposure.

A variation on this method of preventing unwanted UV exposure entails implementing an electrical safety switch that prevents operation of the UV light source unless the UV light source is properly inserted in the shoe. When positioned correctly, the UV light source closes an electrical circuit, causing actuation of the safety switch to an operating condition that allows a user to activate the light source. Alternatively, instead of using a traditional switch, a tilt switch, a motion sensor, an accelerometer, or similar movement sensing device capable of detecting whether the UV light source changes its position while activated can be used to deactivate the light source upon its movement to prevent the user from being exposed to the light.

A further method of safeguarding the user from unwanted exposure to UV light entails placing the shoe inside a container. The container is made of translucent, opaque, or transparent material that absorbs at least some of the UV light emanating from the interior of the shoe. Use of a container may be combined with the aforementioned light sensor to reduce the intensity of ambient light inside the shoe, provided that the container is translucent or opaque. This is a preferred method of treating sandals or open-toed shoes with germicidal UV light while reducing risk of unwanted UV exposure.

Another embodiment, in addition to providing the light source to the interior of the footwear, circulates forced air through the footwear to help dry it. The air circulation may incorporate a filtration system to reduce the odor in the footwear.

Yet another embodiment uses a titanium dioxide ($TiO_2$) coating on parts located adjacent the UV lamp. The UV lamp will cause a photocatalytic reaction with the titanium dioxide to sanitize the air. A preferred implementation of this embodiment also incorporates a fan or other device to circulate air to cause the airborne pathogens to come in contact with the surfaces coated with titanium dioxide.

Still another embodiment uses a photocatalytic oxidation coating on surfaces inside the interior region of the footwear. A light source illuminating the coated interior region of the footwear activates antimicrobial properties of the coating to provide an effective germicide for sanitizing the footwear.

Additional aspects and advantages will be apparent from the following detailed description of preferred embodiments, which proceeds with reference to the accompanying drawings.

BRIEF DESCRIPTION OF THE DRAWINGS

FIGS. 2A and 2B are bottom and top isometric views, respectively, of a second preferred embodiment of a shoe tree, in which an ultraviolet germicidal bulb is installed.

FIGS. 3A, 3B, 3C, 3D, and 3E are, respectively, top plan, right-hand side, left-hand side, rear, and front elevation views of the shoe tree shown in FIGS. 2A and 2B.

FIG. 3F is a front perspective view of the shoe tree shown in FIGS. 2A and 2B.

FIG. 3G is a sectional view taken along lines 3G-3G of FIG. 3A.

FIGS. 9A, 9B, and 9C are diagrams of safety enclosures that prevent light leakage from a shoe sanitizer installed in a shoe.

FIGS. 10A and 10B are pictorial side elevation views showing different sides of a first embodiment of an integrated footwear sanitizing and deodorizing system in, respectively, a folded state and an unfolded state.

FIG. 11 is a pictorial frontal view showing the air flow channel of the air hose in the sanitizing and deodorizing system of FIGS. 10A and 10B.

FIGS. 12A, 12B, and 12C are diagrams showing installation of the sanitizing and the deodorizing system of FIGS. 10A and 10B in pairs of, respectively, high top shoes, slip-on loafers, and riding boots.

DETAILED DESCRIPTION OF PREFERRED EMBODIMENTS

Figure 1:
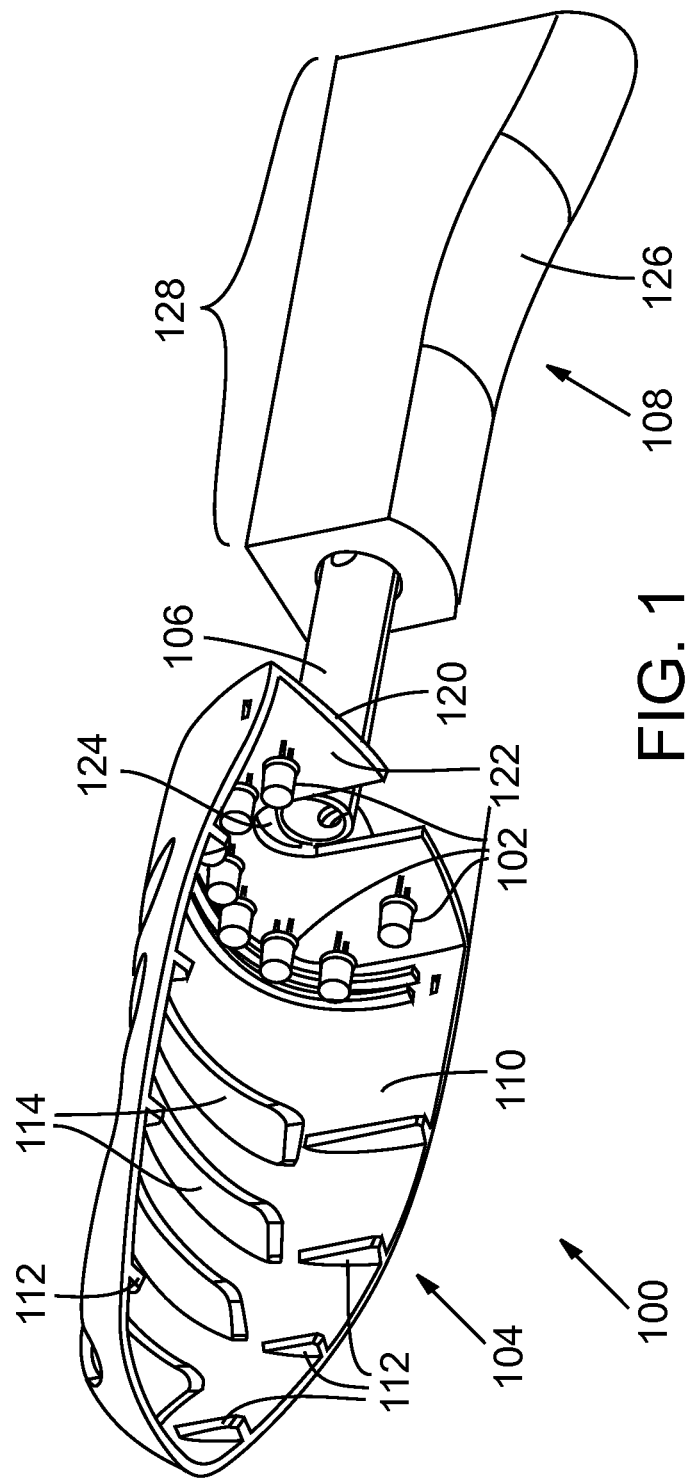
FIG. 1 is an isometric view of a first preferred embodiment of a shoe tree, as seen from underneath a hollow forepart of the shoe tree to show placement of light emitting diodes ("LEDs").

FIG. 1 shows, as a first embodiment, a shoe tree 100 configured to accommodate a semi-circular linear array of LEDs 102 that, in a preferred embodiment, radiate germicidal UV light, or white light including a UV component, into the toe of a shoe in which shoe tree 100 is inserted. A UV LED that emits light within the germicidal range and is suitable for use in LED array 102 is a Model No. UVTOP255-BL-TO39, available from Roithner LaserTechnik, Vienna, Austria. Visible light (blue or white) LEDs, which are readily available, can be used to inhibit or prevent further growth of microorganisms in the shoe. Shoe tree 100 includes a hollow forepart 104 connected by an extensible one-piece cylindrical spine 106 to a heel section 108.

Forepart 104 is a curved half-shell structure having an inner surface 110 that supports multiple inwardly directed, spaced-apart structural tabs 112 and having multiple generally rectangular, elongated slots 114 that are spaced apart in a transverse direction to the length of forepart 104. Light emitted by LED array 102 propagates through elongated slots 114 and impinges directly on the interior lining of the upper of a shoe (not shown) in which shoe tree 100 is placed. Because forepart 104 of shoe tree 100 is hollow, the interior footed of the shoe is illuminated by LED array 102. A wall 120 defines a back end of forepart 104 and has an interior surface 122 on which LED array 102 is mounted. Light emitted by LED array 102 propagates primarily in a forward direction toward the toebox of the shoe. A half-oval cutout 122 in wall 120 allows cylindrical spine 106, which extends out of and retracts into the interior of heel section 108, to extend into the toebox of the shoe, or retract to the middle of the shoe, as needed to adjust the overall length of shoe tree 100 to fit a particular shoe. Heel section 108 of shoe tree 100 is of a design found in a conventional shoe tree. Heel section 108 is in the shape of a modified solid rectangular block, with a rounded lower surface 126, in which the depth 128 of the solid block becomes gradually thicker from front to rear, to better conform to the heel of a shoe. The bottom of heel section 108 may be scored twice, dividing its surface lengthwise into three sections.

FIGS. 2A, 2B, 3A-3G, and 4-7 show, as a second embodiment, a sanitizing shoe tree 200 in which a UV germicidal bulb 202 is installed, instead of LED array 102 used in shoe tree 100. Shoe tree 200 includes a hollow forepart 204 connected by a spring-loaded extensible spine 206 to a heel section 208. Electronic components enabling UV safety features are concealed throughout heel section 208, spine 206, and hollow forepart 204 and are, therefore, not apparent from the exterior of shoe tree 200. Heel section 208 terminates in a closed loop-shaped handle 210 to facilitate length adjustment; spring-loaded extensible spine 206 allows linear motion into and out of heel section 208; and hollow forepart 204 features large openings, or windows, of non-uniform size and shape through which light can propagate into the interior of a shoe. A power supply cord 212 extends from the rear of heel section 208 and provides electrical power for delivery to UV germicidal bulb 202 as described below. The top of handle 210 includes a power-on button 214, which activates the UV bulb along with its safety checks. The manufacture of shoe tree 200 may incorporate a scent into the material by impregnating it with a liquid, a solid, or a gel. For example, shoe tree 200 could be constructed from a scented polymer such as that used in the manufacture of AURACELL products by Rotuba, Linden, N.J.

With particular reference to FIG. 3A, forepart 204 is formed by two skeletal sections, including a left-hand side skeletal section 218 and a right-hand side skeletal section 220. Skeletal section 218 has from front to back an approximately triangular-shaped window 222 and a generally parallelogram-shaped window 224. Skeletal section 220 has from front to back generally parallelogram-shaped windows 230, 232, and 234.

FIG. 3A shows the asymmetric design of hollow forepart 204 of shoe tree 200. Windows 224 and 234 are symmetric about a central longitudinal axis 238, which runs along the seam of skeletal sections 218 and 220 when they are assembled together. Central longitudinal axis 238 extends straight through the instep of shoe tree 200, angling sideways at approximately 60° in the toe area, causing the foremost window openings 222 and 230, to be irregularly shaped. A pair of shoe sanitizers includes left-hand and right-hand shoe trees, the left-hand shoe tree configured in a mirror image of right-hand shoe tree 200 shown in FIG. 3A.

Figure 4:
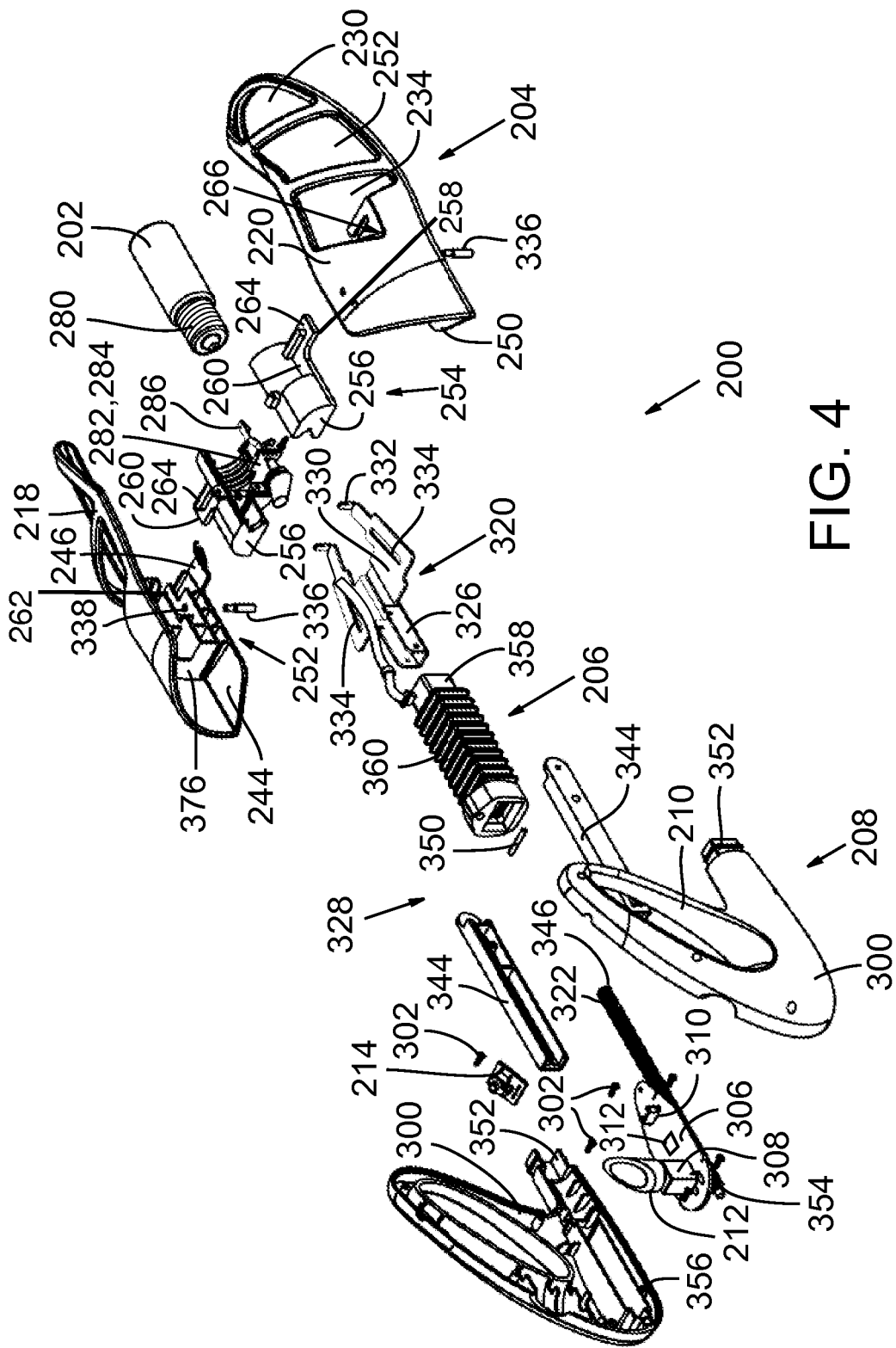
FIG. 4 is an exploded view of the shoe tree shown in FIGS. 2A and 2B.

With particular reference to FIG. 4, skeletal section 218 has a floor portion 244 from which a tab member 246 extends and contacts a tab member 248 that extends from a floor portion 250 of skeletal section 220 (see also FIG. 3G). Tab members 246 and 248 form a smooth surface region when skeletal sections 218 and 220 are assembled together at the bottom of hollow forepart 204. Skeletal sections 218 and 220 support on their respective floor portions 244 and 250, mounting blocks 252 that are sized to receive and support a split bulb carrier 254. Split bulb carrier 254 is an assembly of matable half sections 256, from which T-shaped projections 258 extend. Base portions 260 of T-shaped projections 258 mate with slots 262 of complementary shape formed in corresponding mounting blocks 252 to hold split bulb carrier 254 in place when skeletal sections 218 and 220 are assembled together. Tabs 264 extending upwardly from base portions 260 of half sections 256 of bulb carrier 254 accommodate a width adjustment of hollow forepart 204, by constraining sideways motion of moveable skeletal sections 218 and 220 within their associated slots 266, one of which is shown in FIGS. 2B and 4.

Split bulb carrier 254 forms a threaded socket that receives a threaded base 280 of germicidal bulb 202 and a carrier for a small electrical circuit board 282 on which is mounted an electronic ambient light sensor 284. A suitable UV germicidal bulb 202 is a Model No. GTL3, available from Ushio, Inc., Cypress, Calif. An ambient light sensor 284 suitable for use in shoe tree 200 is a Model No. LX1972IBC-TR, available from Microsemi, Irvine, Calif. A pair of leaf springs 286 attached to the front of circuit board 282 ensures contact to the positive and negative terminals of UV germicidal bulb 202. The output signal of ambient light sensor 284 controls initial activation of a sanitizing operation of shoe tree 200 and is, therefore, active for a momentary portion of the sanitizing operation. The output signal is delivered through a cable 288 to heel section 208.

A preferred implementation of sanitizing shoe tree 200 entails applying to its components located adjacent germicidal bulb 202 a titanium dioxide coating, which causes a photocatalytic reaction with UV light emitted by germicidal bulb 202. Airborne pathogens contacting the surfaces coated with titanium dioxide are killed, thereby sanitizing the air in the vicinity of germicidal bulb 202. Surfaces preferably coated with titanium dioxide include outer front surfaces 256f and curved outer surfaces 256c of half sections 256 of split bulb carrier 254 (FIG. 3F) and base portion tab-receiving members 266r of the interiors of skeletal sections 218 and 220 (FIGS. 3A and 3F).

Figure 5:
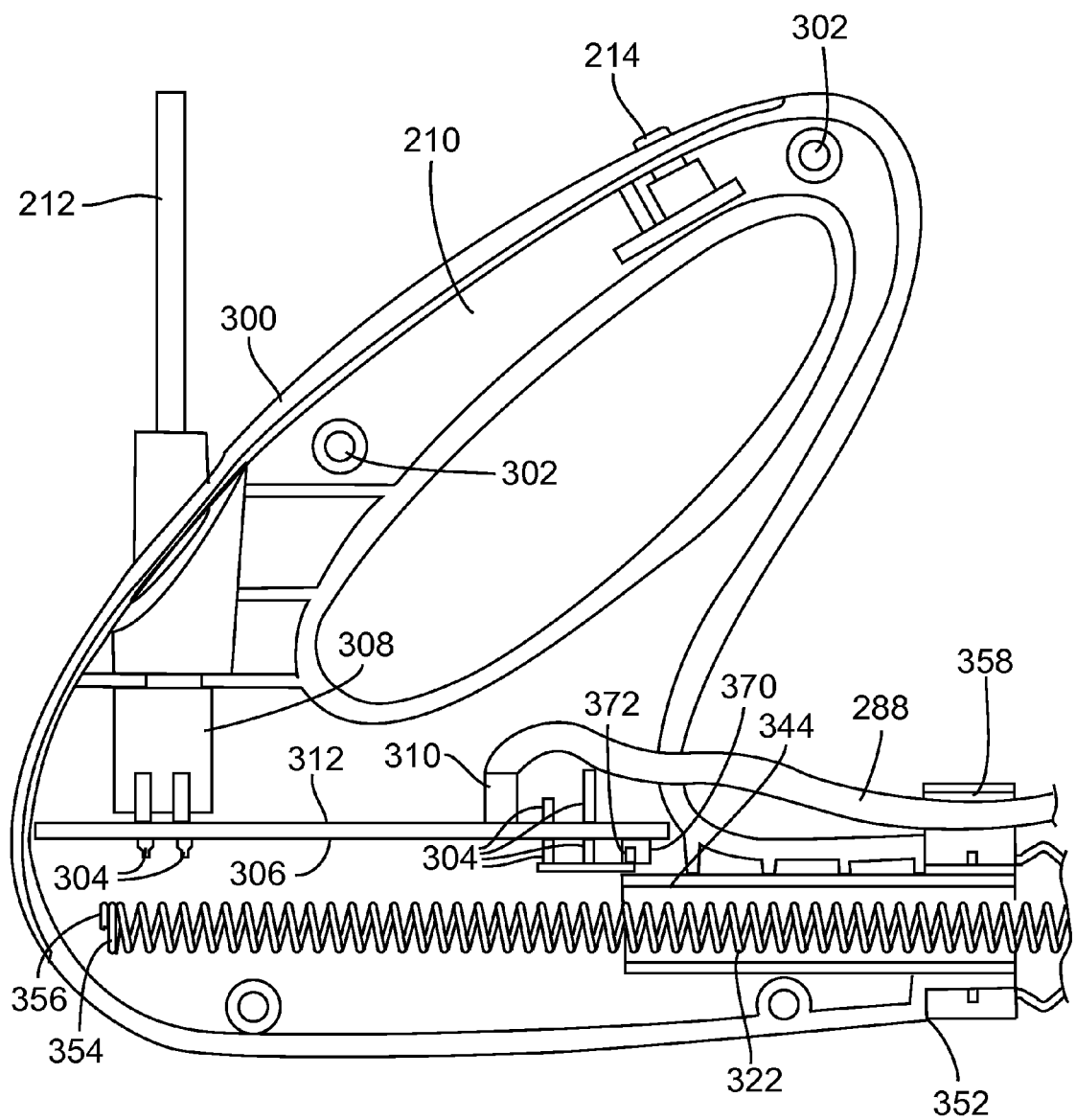
FIG. 5 is an enlarged, fragmentary sectional side elevation view of the heel section of the shoe tree shown in FIGS. 2A and 2B.

With particular reference to FIGS. 4 and 5, heel section 208 is an assembly of matable half-shell sections 300, which are held together by screws 302. Each half-shell section 300 has interior mounting tabs 304 that support an electrical circuit board 306 in position below and along the length of the bottom part of handle 210. Circuit board 306 provides a connection point 308 in the form of a power supply for power supply cord 212 and a connection point 310 for cable 288. Circuit board 306 carries a microcontroller 312 that controls the operation and safety functions implemented in shoe tree 200. Microcontroller 312 controls through cable 288 delivery of electrical power to UV germicidal bulb 202 and processing of the output signal of ambient light sensor 284. Spring-loaded adjustable spine 206 includes at its forward end a skeletal section spread plate 320 terminating in hollow forepart 204 and at its rear end a long coil spring 322 terminating in heel section 208.

FIG. 4 shows a clevis 326 at an end of spread plate 320 and a spring carrier 328. Spread plate 320 has a support surface 330 on which half sections 256 of split bulb carrier 254 rest. Upright end tabs 332 of spread plate 320 hold split bulb carrier 254 in place by restricting its forward movement as spine 206 undergoes changes in length. Two guide slots 334 in spread plate 320 converge in a forward direction toward the toe end of forepart 204. Stepped guide pins 336 pass through guide slots 334 in spread plate 320 and holes 338 in mounting blocks 252 of skeletal sections 218 and 220 to secure spread plate 320 to skeletal sections 218 and 220 and spread them apart in response to a shortening of spine 206. Spread plate 320 is positioned in forepart 204 so that UV germicidal bulb 202 is set at a fixed distance of 5 cm from the end of a shoe in which shoe tree 200 is installed. The reason for such bulb placement is that the intensity and therefore the effectiveness of UV energy as a sanitizing agent decreases with distance away from the light source. Spring carrier 328, which is formed of two matable U-shaped rails 344, contains and secures in its interior an end 346 of coil spring 322. Spring carrier 328 is fixed by a pin 350 to clevis 326 of spread plate 320.

FIG. 5 shows coil spring 322 passing through a tubular housing portion 352 in the forward end of heel section 208 and an end 354 of coil spring 322 resting against a stop 356 in the rear end of heel section 208. Coil spring 322 is held in a nominal partly compressed state in spine 206. A strain relief clamp 358 holds cable 288 in position on housing portion 352 of heel section 208 as spine 206 undergoes changes in length. An articulated rubber sleeve 360 positioned between forepart 204 and heel section 208 fits over spring carrier 328 and conceals it from view.

Figure 6:
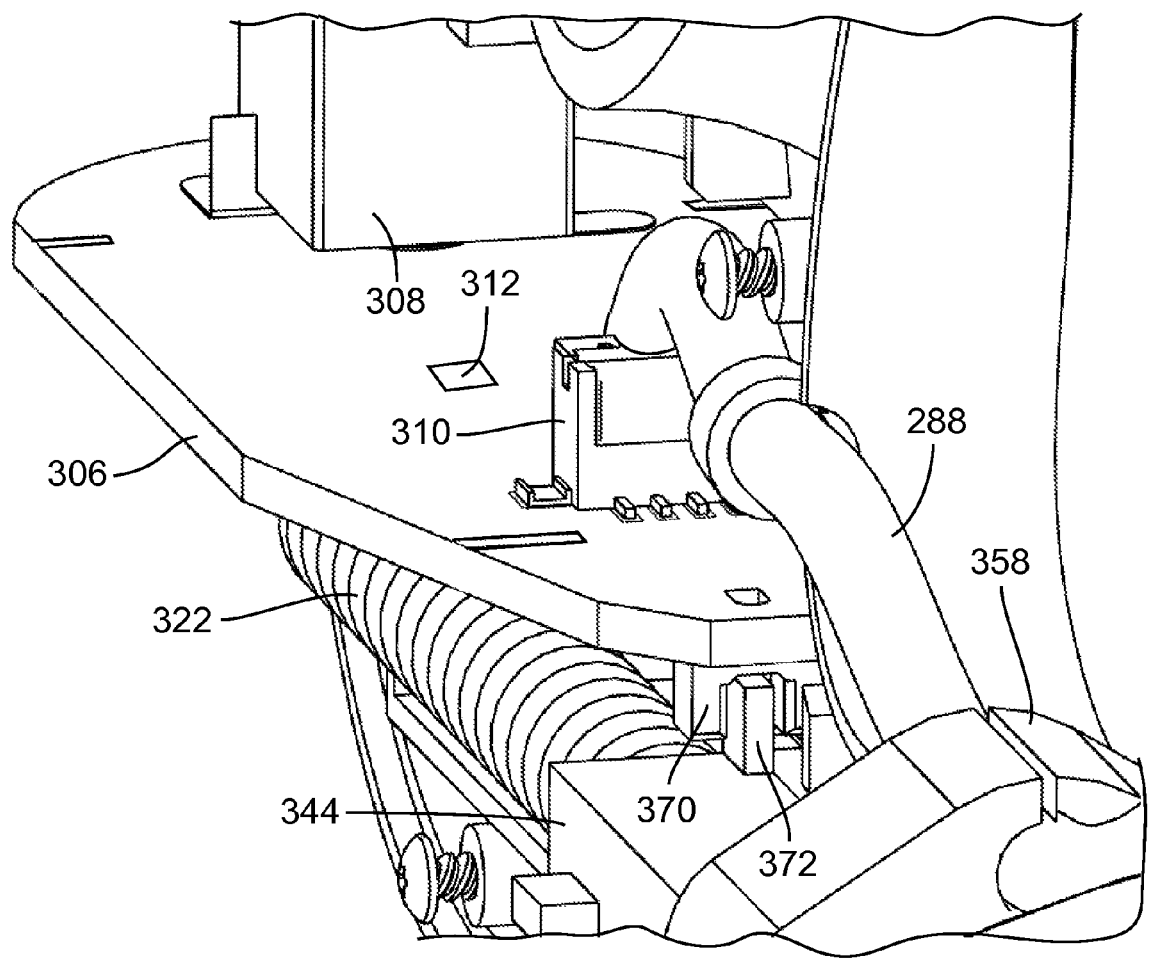
FIG. 6 is an enlarged, fragmentary isometric view of the safety interlock switch in the heel section of the shoe tree shown in FIGS. 2A and 2B.

FIGS. 5 and 6 show a photo-interrupter implemented as a safety switch 370, which includes a spaced-apart infrared (IR) transmitter/detector pair. A fin 372 attached to the back end of U-shaped rail 344 obstructs IR light emitted by the transmitter from reaching the receiver when coil spring 322 is in its nominal partly compressed state. Compression of spring 322 as shoe tree 200 is placed in a shoe causes fin 372 to move rearward, thereby allowing IR light to reach the detector. The output signal from photo-interrupter 370 is sent to microcontroller 312 on circuit board 306 to enable application of power to UV germicidal bulb 202 through cable 288. A suitable photo-interrupter 370 is Part No. GP1S092HCPIF, available from Sharp Electronics Corporation, Romeoville, Ill.

One alternative implementation of safety switch 370 includes use of a tilt sensor or an accelerometer to detect motion dislodging or misaligning the light emission beam path of UV germicidal bulb 202. One suitable accelerometer is a model LIS 302 DL, available from STMicroelectronics, Geneva, Switzerland.

Figure 7:
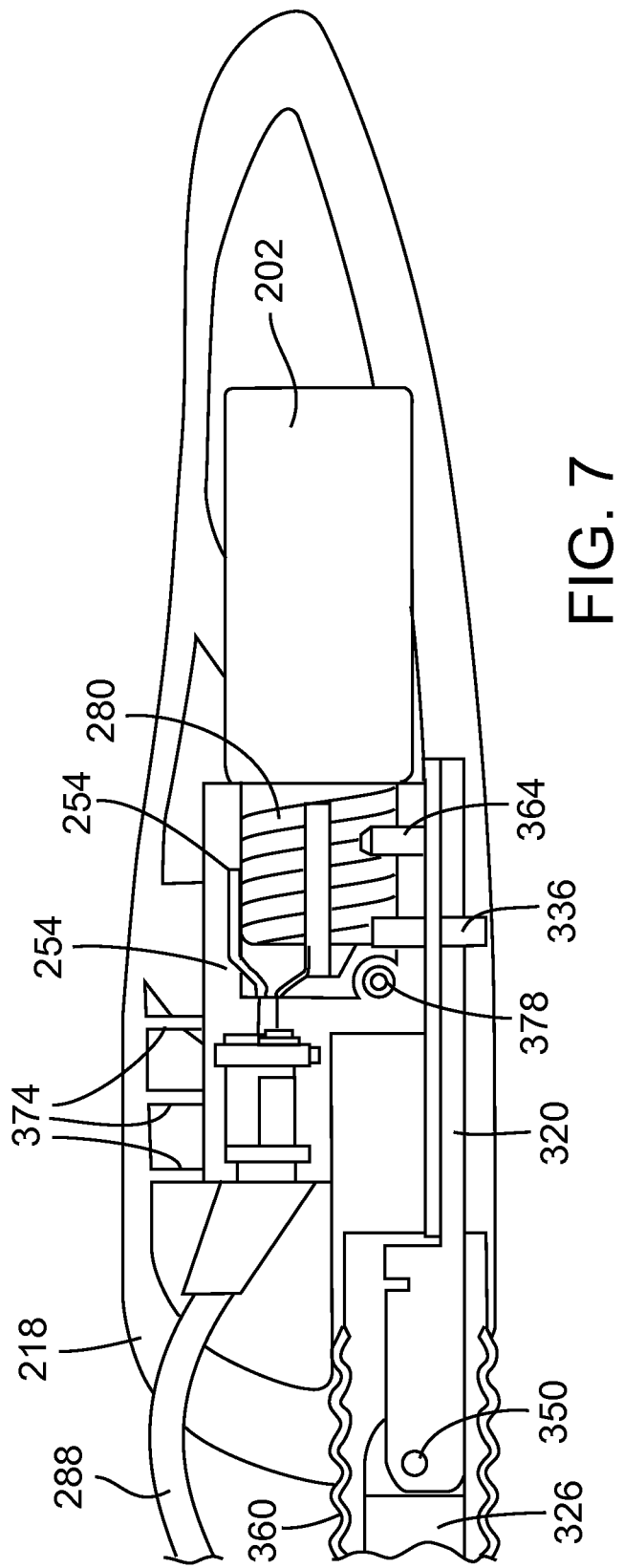
FIG. 7 is an enlarged, fragmentary sectional side elevation view of the hollow forepart of the shoe tree shown in FIGS. 2A and 2B.
Figure 8:
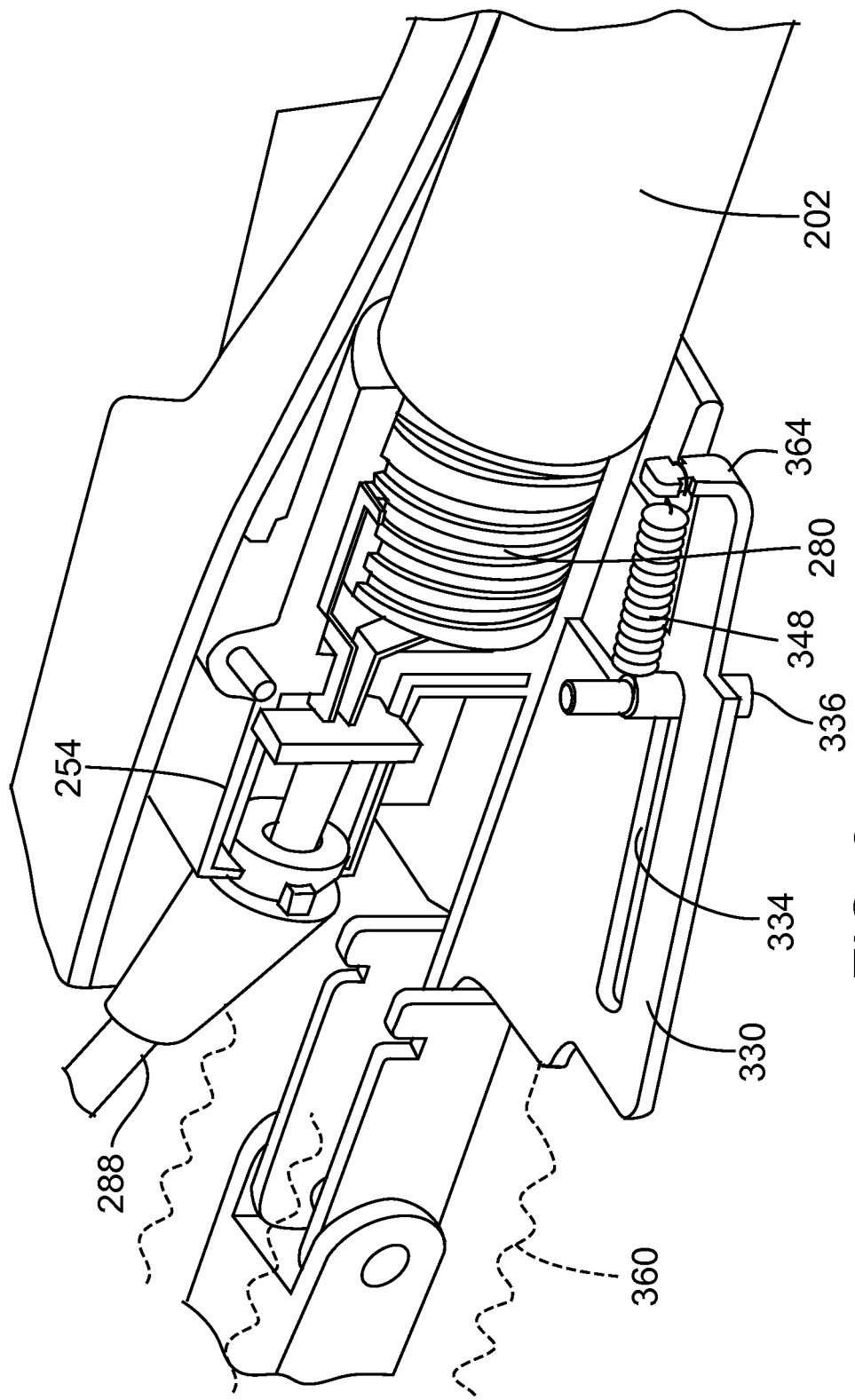
FIG. 8 is an enlarged, fragmentary pictorial view of a width adjustment mechanism in the forepart of the shoe tree shown in FIGS. 2A and 2B.

FIGS. 7 and 8 show the front end of cable 288 where it plugs into split bulb carrier 254 securing UV germicidal bulb 202. Three parallel ribs 374 acting as structural supports for hollow forepart 204 extend downward from the top interior surface of skeletal section 220. FIG. 7 shows ribs 374 positioned above the exterior surface of split bulb carrier 254, together with two vertical bulkheads 376 (FIG. 3G) positioned on either side of rubber sleeve 360 covering spine 206, to block light from escaping the toe of the shoe. With reference to FIG. 8, for each of skeletal sections 218 and 220, a coil spring 348 is positioned between a spring tensioner post 364 and guide pin 336 to hold skeletal sections 218 and 220 together when shoe tree 200 is not placed in a shoe. (In FIG. 8, only one coil spring 348 appears, and it is shown disconnected from spring tension post 364.) Spring tensioner post 364 and guide pin 336 are positioned outside of threaded base 280 of UV germicidal bulb 202. Guide pin 336 restricts lateral displacement of skeletal section 220. The end of a circular rivet 378 joining half sections 256 of split bulb carrier 254 is visible in FIG. 7, along with pin 350 located in clevis 326 at the rear of spread plate 320. Pin 350 forms a pivot point allowing spine 206 to articulate upward relative to forepart 204.

Adjustment of the length of spine 206 to place shoe tree 200 in a shoe is accomplished by a user grasping handle 210 and positioning forepart 204 in the toe box of the shoe. The user then exerts pressure on heel section 208 to compress coil spring 322, while lowering heel section 308 into the heel of the shoe. Compressing coil spring 322 shortens spine 206 and thrusts spread plate 320 forward, thereby separating skeletal sections 218 and 220, and producing a snug fit of shoe tree 200 in the shoe so that UV light will not escape from it.

After shoe tree 200 is positioned inside a shoe, application of electrical power through power supply cord 212 by actuation of power-on button 214 triggers the following sequence of events to protect user safety: A preliminary ambient light check is initiated using light sensor 284 to ensure UV source 202 is contained within the shoe with no detected light leaks. If the ambient light check is negative (i.e., no appreciable light leakage detected), a heel compression check using photo-interrupter 370 acting as an electrical safety switch is initiated to ensure that shoe tree 200 is properly positioned within a shoe. If the heel compression check is positive (i.e., improper shoe tree installation not detected), microcontroller 312 engages UV light source 202 to sanitize the shoe for approximately 30 minutes. If during a 30-minute shoe sanitization operating window shoe tree 200 is removed or dislodged from the shoe, safety switch 370 deactivates the UV light source 202. The forepart ambient light check using sensor 284 is not active during the 30-minute operating window.

An alternative embodiment without use of a shoe tree lends itself to commercial use and prohibits, by blocking the escape of UV radiation during a shoe sanitization operating window, the UV light from reaching an individual who is proximally located to the shoe. This alternative embodiment entails inserting a UV lightbulb into a shoe and either surrounding the shoe with a protective "shower cap," enclosing the shoe in a protective bag, or sealing the opening of the shoe.

Figure 9A:
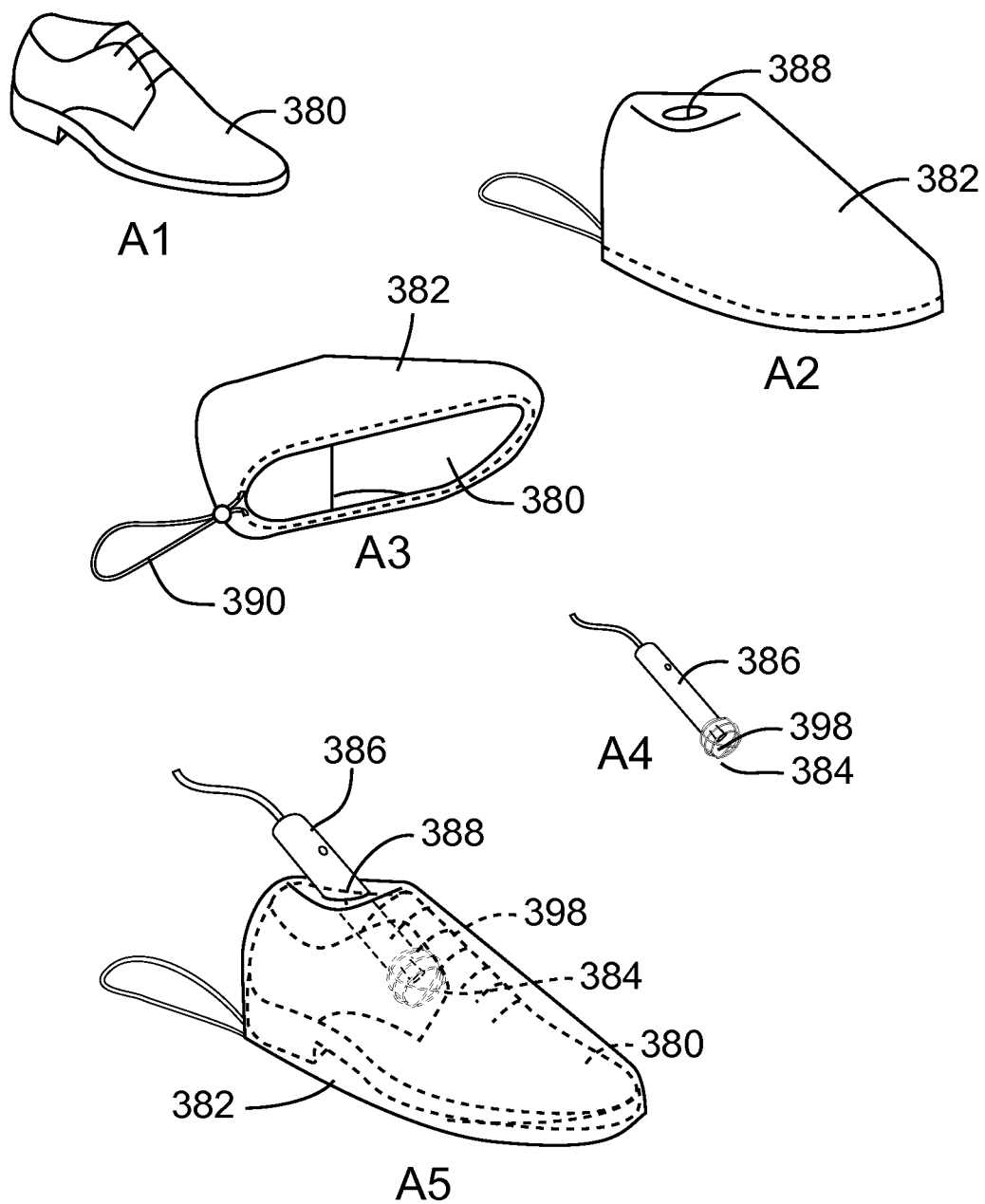
Figure 9B:
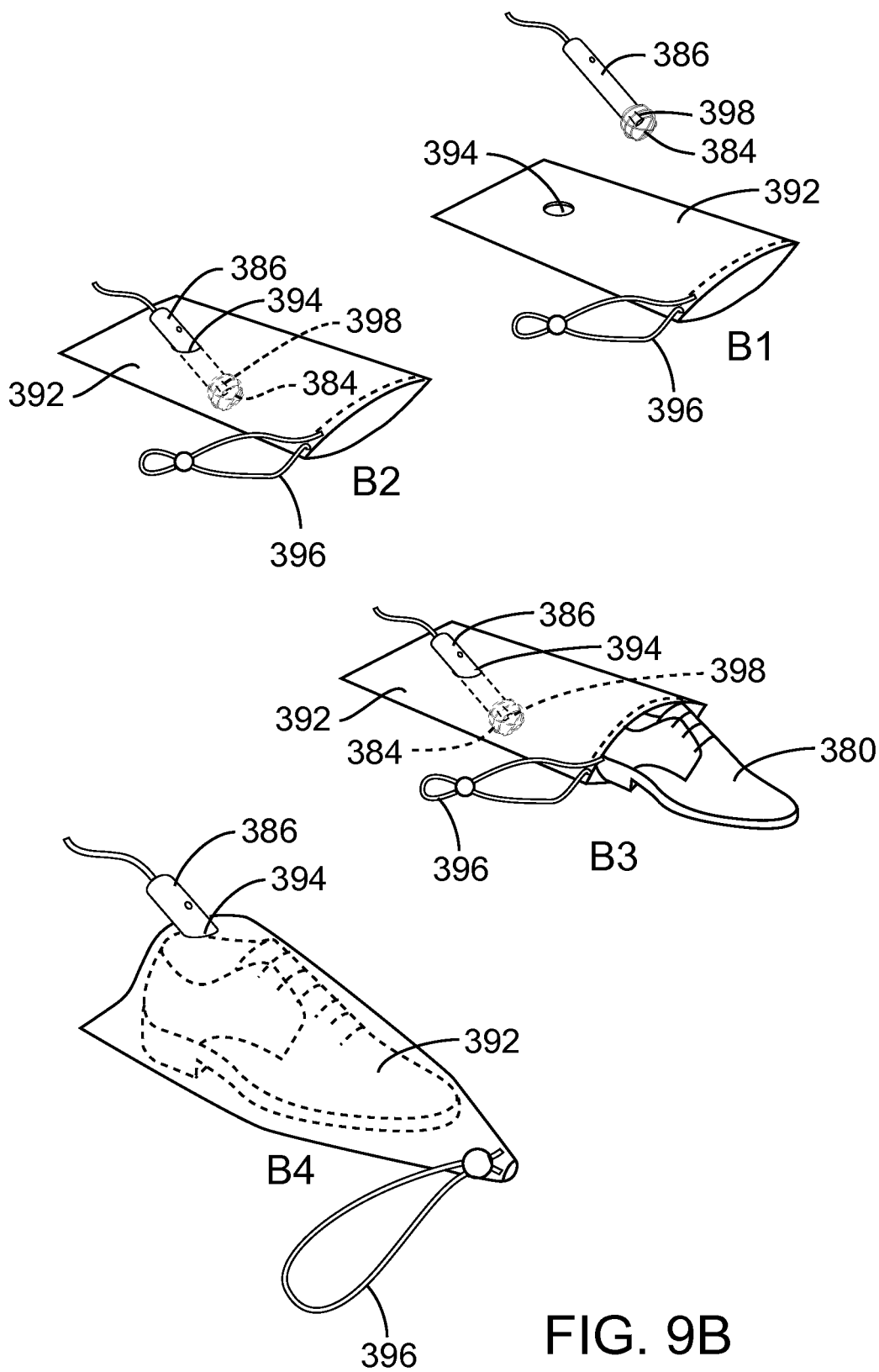

More specifically, FIG. 9A shows a series of images that illustrate enclosing a shoe 380 (image A1) in a shower cap style enclosure 382 (images A2 and A3) and inserting a UV lightbulb 384 attached to a long, cylindrical handle 386 (image A4) through an opening 388 in enclosure 382 into the inside of shoe 380 (image A5). Enclosure 382 is secured around shoe 380 by tightening a drawstring 390. FIG. 9B shows a series of images that illustrate enclosing shoe 380 in a closed bag 392 (image B1). UV lightbulb 384 attached to handle 386 is inserted in an opening 394 in bag 392 (image B2) and into the inside of shoe 380 (images B3 and B4). Bag 392 is secured around shoe 380 by tightening a drawstring 396 that closes the open side of bag 392.

Both enclosure 382 and bag 392 are made of a UV light-blocking material. UV lightbulb 384 may be enclosed in a protective metal mesh cage 398.

FIG. 9C shows a series of images that illustrate an alternative to full enclosure of shoe 380 by sealing the open top of shoe 80 with a cap 400 (image C1). Cap 400 has an opening 402 through which UV light bulb 384 attached to handle 386 is inserted (image C2). Disassembly of UV light bulb 384 and cage 398 from handle 386 is carried out to enable its passage through opening 402 and cap 400 (image C3).

FIGS. 10A and 10B show, as a first embodiment in respective folded and unfolded states, a portable integrated footwear sanitizing and deodorizing system 500 in which a centrally located blower fan module 502 is connected at either of its output ends to an integrated air discharge outlet and UV light emission member 504. Each member 504 includes a flexible fluid conduit or hose 506 that is connected to an output end of fan module 502 and terminates in an outer housing 508 perforated with multiple openings 510 and containing a tubular UV germicidal bulb 512 held in a socket 514. Outer housing 508 is configured to fit through the opening and into the interior region of a shoe or other footwear. Fan module 502 produces forced air stream flow through hoses 506. Each hose 506 delivers air stream flow into the outer housing 508 to which the hose 506 is connected and directs the air stream flow in the space between bulb 512 and outer housing 508 for discharge out of its openings 510 and its outlet opening 510o to dry the footwear into which outer housing 508 is inserted.

FIG. 11 shows an air flow channel 516 produced by an apertured fitting 518 positioned at each end of hose 506. FIGS. 12A, 12B, and 12C show members 504 fitted inside the right and left ones of pairs of, respectively, high top shoes 520, slip-on loafers 522, and riding boots 524.

With particular reference to FIG. 10B, a control switch 526 provided on fan module 502 gives user selection of operating modes, and a set of LEDs 528 indicates the selected operating mode of system 500. For example, a user can set control switch 526 to a mode with UV light emission and the fan ON, a mode with UV light emission ON without the fan, a mode with UV light emission ON for preset light emission time, a mode with only the fan ON, a mode with the fan constantly ON and UV light emission cycling ON and OFF at a predetermined time interval, or a mode with UV light emission and the fan OFF, each operating mode indicated by a corresponding number of illuminated LEDs in a thermometer code scheme.

Figure 13:
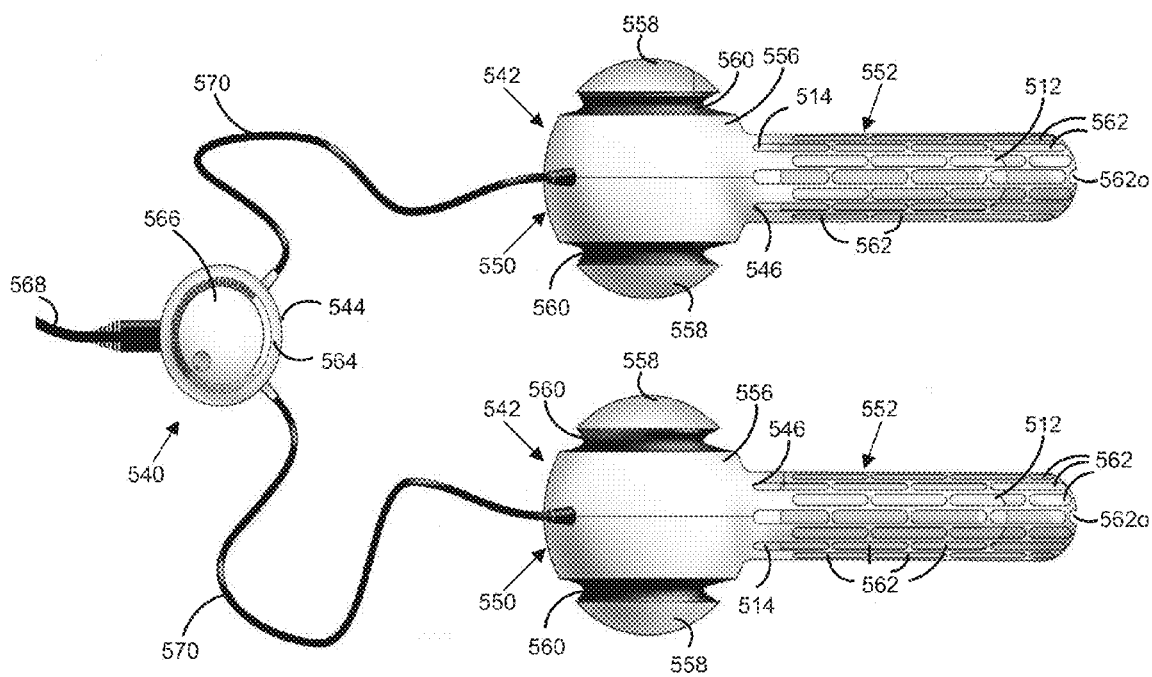
FIG. 13 is a top plan pictorial view of a second embodiment of an integrated footwear sanitizing and deodorizing system that includes two probes configured for insertion in separate ones of a pair of shoes.
Figure 14:
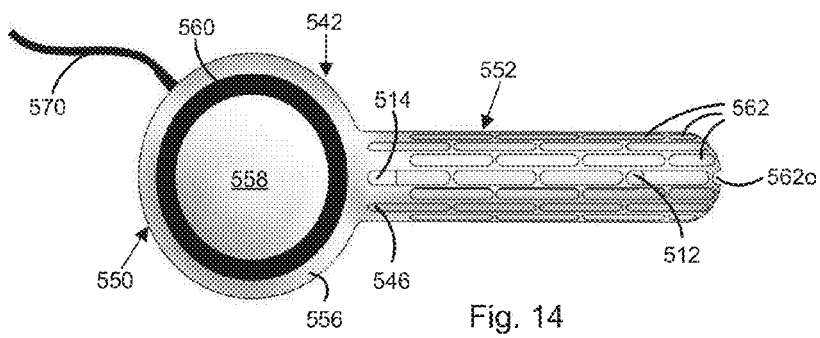
FIG. 14 is a pictorial side elevation view of one of the probes of the sanitizing and deodorizing system of FIG. 13.

FIGS. 13 and 14 show, as a second embodiment, an integrated footwear sanitizing and deodorizing system 540 that includes a pair of similar gavel-shaped probes 542 electrically connected to a controller 544. Each of probes 542 is equipped with a blower fan 546 and a tubular UV germicidal bulb 512 and is configured to fit through an opening 548 (FIGS. 15A, 15B, and 15C) and into the interior region of a shoe or other footwear.

Each probe 542 has an arm 550 and a perforated hollow stem 552. Arm 550 houses fan 546 and socket 514 to which bulb 512 is connected. Arm 550 has a body 556 on opposite ends of which are mounted hemispherical shells or contact balls 558. Contact balls 558 are extensible along the length of body 556 to fit against the inside surface of and thereby secure in place probe 542 inside the footwear. When they are not compressed by the inside surface of the footwear, contact balls 558 may actuate a safety switch (not shown) housed within arm 550 to disable UV light emission from bulb 512. Rubber sleeve boots 560 provide a UV light-escape prevention connection between contact balls 558 and body 556. Hollow stem 552 is perforated with multiple openings 562 through which light emissions from bulb 512 and forced air produced by fan 546 can pass. In this embodiment, fan 546 can be of a type that either discharges air or draws in air to produce forced air flow. Forced air produced by fan 546 flows in the space between bulb 512 and hollow stem 552 along its length and out of its openings 562 and its outlet opening 562o to dry the footwear article into which probe 542 is inserted.

With particular reference to FIG. 13, controller 544 includes a housing 564 to which a rotary dial 566 is mounted for user selection of which ones or both of probes 542 are to be operated. An electrical power cord 568 delivers 120 VAC to controller 544, and electrical wires 570 are routed from housing 564 to separate ones of probes 542.

Figure 15A:
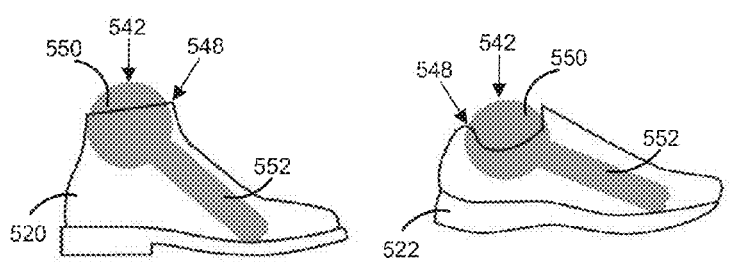
FIGS. 15A, 15B, and 15C are diagrams showing one of the probes of the sanitizing and deodorizing system of FIG. 13 inserted in, respectively, a high top shoe, slip-on loafer, and riding boot.
Figure 15B:
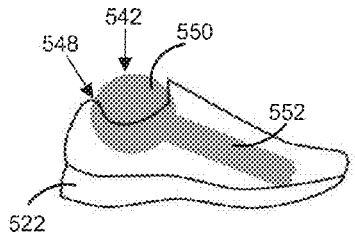
Figure 15C:
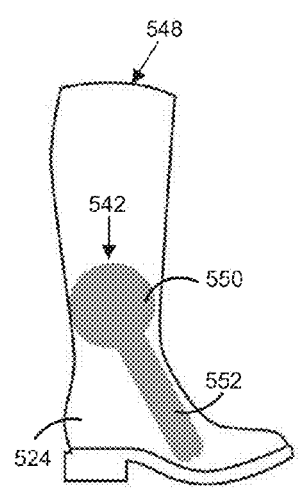

FIGS. 15A, 15B, and 15C show probe 542 installed in, respectively, high top shoe 520, slip-on loafer 522, and riding boot 524. Contact balls 558 of probe 542 partly occlude opening 548 in the footwear article to allow forced air to escape from the opening and thereby promote air flow through the footwear.

Another embodiment uses a photocatalytic oxidation coating on surfaces inside interior region 104 or 204 of footwear article 100 or 204, respectively. LED light source 102 or UV light source 202 illuminating the coated interior region of the footwear article activates antimicrobial properties of the coating to provide an effective germicide for sanitizing the footwear. Although such coatings are light-activated, most shoe constructions occlude light from reaching the surfaces inside the interior region. Therefore, use of light-activated coatings on these surfaces would not activate until the coatings are exposed to light from the light source placed inside the footwear.

One example photocatalytic oxidation coating is OxiTitan Visible Light Response, which is available from EcoActive Surfaces, Inc. of Pompano Beach, Fla. OxiTitan Visible Light Response is a liquid formulation including titanium dioxide ($TiO_2$) that can be readily sprayed or wiped with a towel onto shoe interior surfaces.

Shoe interior coatings are exposed and activated by visible light delivered from LED array 102 of shoe tree 100 (FIG. 1), or by UV light delivered from UV light bulb 384 (FIG. 9A) or tubular UV germicidal bulb 512 (FIG. 10A). In other embodiments, visible or UV light may be delivered by an LED or a bulb mounted in a housing having a transparent or translucent exterior surface that is sized to snuggly fit, roll, or slide within the shoe interior. For example, the housing exterior surface may be partly or completely spherical, according to some embodiments. Previously described enclosure 382 (FIG. 9A), bag 392 (FIG. 9B), cap 400 (FIG. 9C), and safety features of FIGS. 10-15 could be omitted when visible light is used to activate the photocatalytic oxidation coating.

It will be obvious to those having skill in the art that many changes may be made to the details of the above-described embodiments without departing from the underlying principles of the invention. The scope of the present invention should, therefore, be determined only by the following claims.

The invention claimed is:

1. Apparatus for sanitizing human footwear having an opening through which a person inserts his foot for placement inside a footwear interior region to put on the footwear, comprising:

a light source emitting radiation in a wavelength range that sanitizes the footwear by inhibiting growth of or destroying microorganisms present in the footwear interior region, the light source having a base;

a hollow forepart shaped to pass through the opening in the footwear and fit inside the footwear interior region, the hollow forepart configured in the form of a skeletal structure that includes multiple windows, and the hollow forepart including a multi-section back end wall having an interior surface that functions as a light block contributing to inhibit the radiation from escaping the footwear undergoing sanitization by the apparatus;

a rear part positioned behind the hollow forepart and delivering electrical power from a power source to activate the light source and generate emission of the radiation; and a support for the light source to set it in a sanitization position to direct the radiation through the hollow forepart to the footwear interior region, the support including a light source receptacle accessible through an opening in the interior surface of the multi-section back end wall and configured to receive the base of the light source in the sanitization position to emit the radiation through the multiple windows.

2. Apparatus for sanitizing human footwear having an opening through which a person inserts his foot for placement inside a footwear interior region to put on the footwear, comprising:

a light sensitive chemical compound applied to surfaces of the footwear interior region;

a light source emitting radiation in a wavelength that reacts with the light sensitive chemical compound to activate the light sensitive chemical compound so that it becomes volatile to microorganisms;

a support for the light source to set it in a position to direct the radiation to the applied light sensitive chemical compound;

a power source to power the light source emitting radiation; and control circuitry providing a temporal operational sequence of sanitizing the footwear, the control circuitry operatively connected to a user-actuated power-on control that initiates a preliminary period defined from user-actuation of the power-on control to activation of the light source, the preliminary period being of sufficient duration to ensure no unwanted exposure to the radiation, and the control circuitry providing a specified operating time window during which the radiation sanitizes the footwear.

3. The apparatus of claim 2, in which the light sensitive chemical composition is titanium dioxide.

4. The apparatus of claim 1, in which the support for the light source includes multiple support sections assembled to receive the base of the light source.

5. The apparatus of claim 4, in which the multiple support sections include matable arcuate half sections and in which, when assembled, the arcuate half sections form the light source receptacle in the shape of a cylinder.

6. The apparatus of claim 1, in which the light source receptacle includes multiple light source carrier sections that are associated with and extend from different sections of the multi-section back end wall.

7. The apparatus of claim 6, in which each of the associated light source carrier sections and sections of the multi-section back end wall are formed as integral structures.

8. The apparatus of claim 1, in which the light source receptacle includes multiple light source carrier sections that are associated with different sections of the multi-section back end wall, and in which each of the associated light source carrier sections and sections of the multi-section back end wall are formed as integral structures.

9. The apparatus of claim 1, further comprising a flexible cover for placement over the footwear so as to limit outside exposure to radiation escaping from the footwear interior region.

10. The apparatus of claim 9, in which the flexible cover envelops the footwear.

11. The apparatus of claim 1, further comprising control circuitry providing a temporal operational sequence of sanitizing the footwear, the control circuitry operatively connected to a user-actuated power-on control that initiates a preliminary period defined from user-actuation of the power-on control to activation of the light source, the preliminary period being of sufficient duration to ensure no unwanted exposure to the radiation, and the control circuitry providing a specified operating time window during which the radiation sanitizes the footwear.

12. The apparatus of claim 9, in which the flexible covering includes an opening for passage of the hollow forepart.

13. The apparatus of claim 9, in which the flexible covering includes an opening for passage of the rear part.

14. The apparatus of claim 9, in which the flexible covering includes an opening for passage of the power source to be connected to the rear part.

* * * * *